United States Patent
Huang et al.

(10) Patent No.: US 10,787,408 B1
(45) Date of Patent: Sep. 29, 2020

(54) METHOD FOR PRODUCING 9,9-BIS(3-PHENYL-4-(2-HYDROXYETHOXY)PHENYL)FLUORENE

(71) Applicant: CHINA PETROCHEMICAL DEVELOPMENT CORPORATION, Kaohsiung (TW)

(72) Inventors: Ding-Chi Huang, Kaohsiung (TW); Yu-Sen Chen, Kaohsiung (TW); Chih-Wei Chang, Kaohsiung (TW); Wei-Ying Li, Kaohsiung (TW)

(73) Assignee: CHINA PETROCHEMICAL DEVELOPMENT CORPORATION, Kaohsiung (TW)

( * ) Notice: Subject to any disclaimer, the term of this patent is extended or adjusted under 35 U.S.C. 154(b) by 0 days.

(21) Appl. No.: 16/787,495

(22) Filed: Feb. 11, 2020

(30) Foreign Application Priority Data

Aug. 27, 2019 (TW) ................. 108130632

(51) Int. Cl.
| | | |
|---|---|---|
| *C07C 41/09* | (2006.01) | |
| *C07C 43/00* | (2006.01) | |
| *B01J 31/00* | (2006.01) | |
| *B01J 31/02* | (2006.01) | |
| *C07C 43/23* | (2006.01) | |

(52) U.S. Cl.
CPC ............ *C07C 41/09* (2013.01); *B01J 31/0222* (2013.01); *C07C 43/23* (2013.01); *C07C 2603/18* (2017.05)

(58) Field of Classification Search
CPC ...... C07C 41/09; C07C 43/23; C07C 2603/18; B01J 31/0222
See application file for complete search history.

(56) References Cited

U.S. PATENT DOCUMENTS 9,193,826 B2 * 11/2015 Shigematsu ........... C08G 63/19

FOREIGN PATENT DOCUMENTS

WO WO-2013133106 A1 * 9/2013 ............. C07C 43/23

* cited by examiner

*Primary Examiner* — Sikarl A Witherspoon
(74) *Attorney, Agent, or Firm* — Kelly & Kelley, LLP

(57) ABSTRACT

A method for producing 9,9-bis(3-phenyl-4-(2-hydroxyethoxy)phenyl)fluorene is provided. The method includes the steps of: performing a condensation reaction with fluorenone and 2-[(2-phenyl)phenoxy]ethanol in the presence of a catalyst and co-catalyst, wherein the catalyst is alkylsulfonic acid, and the co-catalyst is a mercapto-containing compound, thereby effectively reducing the formation of a by-product, such that the product has characteristics of low chroma, high purity, and high yield.

20 Claims, No Drawings

METHOD FOR PRODUCING 9,9-BIS(3-PHENYL-4-(2-HYDROXYETHOXY) PHENYL)FLUORENE

1. TECHNICAL FIELD

The present disclosure relates to methods for preparing 9,9-bis(3-phenyl-4-(2-hydroxyethoxy)phenyl)fluorene, and more particularly, to a method for preparing 9,9-bis(3-phenyl-4-(2-hydroxyethoxy)phenyl)fluorene using alkylsulfonic acid as a catalyst.

2. DESCRIPTION OF ASSOCIATED ART

Bisphenol fluorene derivatives generally have the advantages of heat resistance, transparency, and high refractive index, and can be used as resin materials such as epoxy resins, polyester resins, and polycarbonate resins, and are also widely used in heat-resistant materials and optical materials.

Owing to the good transparency, high thermal stability, high refractive index, etc., the 9,9-bis[3-phenyl-4-(2-hydroxyethoxy)phenyl]fluorene material is an important intermediate for preparing photovoltaic materials, and has recently received much attention from the market.

Compared to other bisphenol fluorene derivatives, the 9,9-bis[3-phenyl-4-(2-hydroxyethoxy)phenyl]fluorene material has a molecular structure modified with an ethoxy group to greatly improve the solvent solubility, so that it can be widely used for the good solubility property.

At present, the existing producing method of 9,9-bis[3-phenyl-4-(2-hydroxyethoxy)phenyl]fluorene is mostly catalyzed by sulfuric acid, but the sulfuric acid is easily sulfonated with organic solvents and 2-[(2-phenyl)phenoxy]ethanol reactant, or produces a sulfonate by-product, which affects the yield and purity of the product. Moreover, the poor solubility of the by-product increases the difficulty of the purification process, and the production cost of the preparation as well.

In view of the above, it is necessary to propose a method for preparing 9,9-bis[3-phenyl-4-(2-hydroxyethoxy)phenyl]fluorene which is effective for reducing the formation of reaction by-products, so as to solve the existing technical problems in the art.

SUMMARY

In order to solve the above problems, the present disclosure provides a method for preparing 9,9-bis(3-phenyl-4-(2-hydroxyethoxy)phenyl)fluorene, which includes: adding a mercapto-containing compound as a co-catalyst to a reaction system containing 9-fluorenone and 2-[(2-phenyl)phenoxy] ethanol; and adding alkylsulfonic acid as a catalyst in a reaction system containing the co-catalyst, so that the 9-fluorenone and the 2-[(2-phenyl)phenoxy]ethanol are subjected to a dehydration condensation reaction to obtain the 9,9-bis(3-phenyl-4-(2-hydroxyethoxy) phenyl)fluorene.

In one embodiment of the present disclosure, a molar ratio of the 2-[(2-phenyl)phenoxy]ethanol to the 9-fluorenone is from 2 to 4.

In another embodiment of the present disclosure, the catalyst is added to the reaction system in batches at a temperature of from 40 to 80° C. For example, the catalyst is added dropwise to the reaction system, and when the catalyst is added, the temperature change of the reaction system is less than 10° C. In still another embodiment of the present disclosure, the molar ratio of the total addition amount of the catalyst to the 9-fluorenone is from 3 to 9.

In one embodiment of the present disclosure, the catalyst is added in multiple stages. For example, after the addition of the co-catalyst to the reaction system, the catalyst is added in a two-stage manner, wherein after the catalyst is added in a first stage, the dehydration condensation reaction is carried out for 4 to 8 hours. Then, the catalyst is further added in an amount in the second stage, and the dehydration condensation reaction is carried out for 4 to 8 hours. In addition, the molar ratio of the total addition amount of the catalyst to the 9-fluorenone is from 3 to 9.

In another embodiment of the present disclosure, the amount of the catalyst added in the first stage is greater than the amount of the catalyst added in the second stage. In other embodiments, the amount of the catalyst added in the second stage may also be greater than the amount of the catalyst added in the first stage.

In one embodiment of the present disclosure, the alkylsulfonic acid has the formula R—SO$_3$H, wherein R is a C1-C3 alkyl group. In another embodiment of the present disclosure, the catalyst is methanesulfonic acid, and the molar ratio of the methanesulfonic acid to the 9-fluorenone is from 3 to 9.

In an embodiment of the present disclosure, the mercapto-containing compound is at least one selected from the group consisting of a mercaptan containing a C1-C10 alkylene group or a C6-C12 arylene group and a mercaptocarboxylic acid containing a C1-C10 alkylene group or a C6-C12 arylene group. For example, the mercaptocarboxylic acid containing a C1-C10 alkylene group or a C6-C12 arylene group is 3-mercaptopropionic acid, mercaptoacetic acid or mercaptobenzoic acid. In another embodiment of the present disclosure, the molar ratio of the co-catalyst to the 9-fluorenone is from 0.05 to 0.2. For example, with respect to 3-mercaptopropionic acid, the molar ratio of the 3-mercaptopropionic acid to the 9-fluorene is from 0.05 to 0.2.

In one embodiment of the present disclosure, the dehydration condensation reaction is carried out at a temperature of from 40 to 80° C. for a reaction time of from 4 to 12 hours.

In an embodiment of the present disclosure, the preparation method of the present disclosure further includes dissolving the 9-fluorenone and the 2-[(2-phenyl)phenoxy] ethanol in a reaction solvent before adding the co-catalyst.

In one embodiment of the present disclosure, the reaction solvent is an aromatic hydrocarbon solvent or a halogenated alkane. The aromatic hydrocarbon solvent includes at least one selected from the group consisting of benzene, toluene, xylene and trimethylbenzene, and the halogenated alkane includes at least one selected from the group consisting of dichloromethane, chloroform and carbon tetrachloride.

In another embodiment of the present disclosure, the reaction solvent is used in an amount of from 10 to 20% by weight, based on the total weight of the 9-fluorenone and the 2-[(2-phenyl)phenoxy]ethanol.

In one embodiment of the present disclosure, the preparation method of the present disclosure further includes performing recrystallization after the dehydration condensation reaction is completed. In the recrystallization step, a mixed solution of methanol and acetone is used as a recrystallization solvent.

In the preparation method of the present disclosure, by using alkylsulfonic acid as a catalyst and a mercapto-containing compound as a co-catalyst, the formation of by-products can be effectively suppressed, and the yield and purity of the product can be improved. The method has high conversion rate, so that in case of a relatively small amount of 2-[(2-phenyl)phenoxy]ethanol reactant, the cost of the raw material can be effectively reduced, and the problem that the reactant needs to be recovered is excluded. The obtained product has the characteristics of low chroma, high purity, high yield and low cost, and has industrial applicability.

DETAILED DESCRIPTION OF THE EMBODIMENTS

The implementations of the present disclosure are described by way of specific embodiments, and a person skilled in the art can readily understand the advantages and functions of the present disclosure. The present disclosure may be implemented or applied by other different methods, and the various details of the present disclosure may be variously modified and changed without departing from the spirit and scope of the present disclosure. In addition, all ranges and values herein are inclusive and combinable. Any value or point falling within the ranges recited herein, such as any integer, may be the minimum or maximum value to derive the lower range and the like.

A method for preparing 9,9-bis(3-phenyl-4-(2-hydroxyethoxy)phenyl)fluorene of the present disclosure is characterized by adding a mercapto-containing compound as a co-catalyst to the reaction system containing 9-fluorenone and 2-[(2-phenyl)phenoxy]ethanol; and adding an alkylsulfonic acid as a catalyst added to the reaction system containing the co-catalyst to carry out a dehydration condensation reaction of the 9-fluorenone and 2-[(2-phenyl)phenoxy]ethanol to obtain the 9,9-bis(3-phenyl-4-(2-hydroxyethoxy)phenyl)fluorene.

Compared to the conventional process, the preparation method of the present disclosure can completely convert the 9-fluorenone reactant by using a smaller amount of 2-[(2-phenyl)phenoxy]ethanol reactant with a high conversion rate, and can effectively reduce the cost of the process raw materials and eliminate the problem of the need to recover the reactants. In one embodiment, the molar ratio of the 2-[(2-phenyl)phenoxy]ethanol to the 9-fluorenone is 2 to 4.

In some embodiments, a molar ratio of the 2-[(2-phenyl)phenoxy]ethanol to the 9-fluorenone can be, and is not limited to, 2.0, 2.1, 2.2, 2.3, 2.4, 2.5, 2.6. 2.7, 2.8, 2.9, 3.0, 3.1, 3.2, 3.3, 3.4, 3.5, 3.6, 3.7, 3.8, 3.9, and 4.0.

In a preferred embodiment, the molar ratio of the 2-[(2-phenyl)phenoxy]ethanol to the 9-fluorenone is from 2 to 2.1.

Preferably, the 2-[(2-phenyl)phenoxy]ethanol used is 2-[(2-phenyl)phenoxy]ethanol having a purity of 98% or more.

Preferably, the 9-fluorenone is a 9-fluorenone having a purity of 95% or more.

The alkylsulfonic acid has a dehydrating property to facilitate a dehydration condensation reaction, wherein the alkylsulfonic acid has a molecular formula of R—$SO_3H$ and R is a C1-C3 alkyl group. Further, the alkylsulfonic acid is preferably methylsulfonic acid. In one embodiment, the methanesulfonic acid and the 9-fluorenone are preferably from 3 to 9.

In other embodiments, a molar ratio of the methanesulfonic acid to the 9-fluorenone can be 3.5, 4, 4.5, 5, 5.5, 6, 6.5, 7, 7.5, 8, or 8.5, but is not limited thereto.

Since the alkylsulfonic acid used in the present disclosure does not readily react with a 2-[(2-phenyl)phenoxy]ethanol or an organic reaction solvent, the sulfonation or sulfonate by-product can be effectively inhibited, such that the formation thereof simplifies the purification process after the reaction, and the yield and purity of the product are improved.

The mercapto-containing compound is a co-catalyst capable of promoting the formation of a reaction intermediate to improve overall selectivity and productivity. The mercapto-containing compound is at least one selected from the group consisting of a mercaptan containing a C1-C10 alkylene group or a C6-C12 arylene group and the mercaptocarboxylic acid containing a C1-C10 alkylene group or a C6-C12 arylene group. In one embodiment, the mercaptocarboxylic acid containing a C1-C10 alkylene group or a C6-C12 arylene group is 3-mercaptopropionic acid, mercaptoacetic acid or mercaptobenzoic acid, and in particular, 3-mercaptopropene acid is preferred. In an embodiment, the molar ratio of the 3-mercaptopropionic acid to the 9-fluorenone is from 0.05 to 0.2.

In other embodiments, the molar ratio of the 3-mercaptopropionic acid to the 9-fluorenone can be 0.06, 0.07, 0.08, 0.09, 0.10 or 0.15, but is not limited thereto.

In the dehydration condensation reaction, in one embodiment, the co-catalyst and the catalyst are simultaneously added to the reaction.

According to the present disclosure, the co-catalyst is first added and then the catalyst is further added, so as to form an intermediate by means of the co-catalyst to control the selectivity of the reaction, reduce the formation of by-products, effectively improve the reaction rate and increase the reaction yield.

In another embodiment, the co-catalyst and the catalyst are continuously added, and the two are added without time interval, that is, the catalyst is added right after the addition of the co-catalyst.

In an embodiment, the catalyst is added in multiple stages at a temperature of from 40 to 80° C. For example, the total addition amount is added by being divided into 10 aliquots, 20 aliquots, 30 aliquots, 40 aliquots, or even 100 aliquots or more, to complete the addition of the catalyst. In one embodiment, it is added to the reaction system in a dropwise manner conventionally known in the art, to sufficiently uniformly contact the reactants by dropping, control the reaction rate, and strictly control the temperature change to prevent the temperature from rising too fast and resulting in a formation of the by-product. In another embodiment, the catalyst is added at a rate of from 0.06 to 0.3 ml/min. Further, when the catalyst was added dropwise, the temperature change of the reaction system was controlled to be less than 10° C.

Unlike the foregoing interval that is not to be reacted for at least 4 hours, in another embodiment, the catalyst is added in multiple stages. For example, after the co-catalyst is added to the reaction system, the catalyst is added in a two-stage manner, thereby suppressing the progress of the side reaction and improving the purity of the product. For example, after the catalyst is added in the first stage and the dehydration condensation reaction is carried out for 4 to 8 hours, the amount of the catalyst of the second stage is further added, and the dehydration condensation reaction is carried out for 4 to 8 hours. Further, in this aspect, a molar ratio of the total addition amount of the catalyst to the 9-fluorenone is from 3 to 9.

In the preparation method of the present disclosure, the condensation reaction may be further carried out in the presence of a reaction solvent. In one embodiment, the reaction solvent is an aromatic hydrocarbon solvent or a halogenated alkane. The aromatic hydrocarbon solvent comprises at least one solvent selected from the group consisting of benzene, toluene, xylene and trimethylbenzene; the halogenated alkane comprises at least one solvent selected from the group consisting of dichloromethane, chloroform and carbon tetrachloride.

In another embodiment, the preparation method of the present disclosure may further include the step of dissolving the 9-fluorenone and the 2-[(2-phenyl)phenoxy]ethanol in the reaction solvent before adding the co-catalyst. The reaction solvent is used in an amount of from 10 to 20% by weight, based on the total weight of the 9-fluorenone and 2-[(2-phenyl)phenoxy]ethanol. Compared with the existing production method in the art, the reaction solvent in the preparation method of the present disclosure is used in a low amount, so that the reaction cost can be reduced and environmental pollution is less likely to occur.

The reaction conditions of the dehydration condensation reaction are carried out at a reaction temperature of from 40 to 80° C. and a pressure of 1 atm, for 4 to 12 hours. If the reaction temperature is too low, the reaction is sluggish; if the reaction temperature is too high, a side reaction occurs, resulting in a decrease in yield.

In other embodiments, the dehydration condensation reaction temperature can be 41, 42, 43, 44, 45, 46, 47, 48, 49, 50, 51, 52, 53, 54, 55, 56, 57, 58 or 59, but not limited thereto. Further, the dehydration condensation reaction temperature is particularly preferably from 40 to 60° C.

After the dehydration condensation reaction, the preparation method of the present disclosure may further include adding an alkaline aqueous solution to remove the catalyst and the co-catalyst to terminate the reaction. In a specific embodiment, the alkali solution of the alkaline aqueous solution is an inorganic base or an organic base such as an alkali metal hydroxide or a carbonate, and other water-soluble organic solvents are added as needed; and it may be treated at a high temperature as needed.

In another embodiment, the alkaline aqueous solution is added at the temperature of dehydration condensation reaction, and the alkaline aqueous solution is an aqueous sodium hydroxide solution, and the reaction system is heated to 80° C. for stirring; filtrating at room temperature after cooling down, and then a crude product of 9,9-bis(3-phenyl-4-(2-hydroxyethoxy)phenyl)fluorene was obtained.

As a purification step, the preparation method of the present disclosure further includes a step of dissolving the crude product 9,9-bis(3-phenyl-4-(2-hydroxyethoxy)phenyl)fluorene in a recrystallization solvent. The recrystallization step is carried out to separate the impurities, so as to obtain the crystal of the target product. The purification step can be repeated a plurality of times, but is not limited thereto.

The recrystallization solvent includes at least one selected from the group consisting of an alcohol solvent, an aliphatic ketone solvent, an ester solvent, and an aliphatic hydrocarbon solvent. In one embodiment, the recrystallization solvent is a mixed solution of methanol and acetone.

The 9,9-bis(3-phenyl-4-(2-hydroxyethoxy)phenyl)fluorene obtained by the above preparation method of the present disclosure has the characteristics of low chroma and high purity, conducive as the raw material to the high-end optical material product.

The present disclosure is further described in detail by way of examples.

Example 1

9-fluorenone (15 g, 83.24 mmole), 2-[(2-phenyl)phenoxy]ethanol (37.45 g, 174.79 mmole) and toluene (13 g) were placed in a reaction flask and heated to about 50 to 55° C. to completely dissolve the above reactants. Then, 3-mercaptopropionic acid (0.88 g, 8.29 mmole) was added, and methanesulfonic acid (40 g, 416.23 mmole) was added dropwise at a constant rate of 0.3 ml/min. After the completion of the dropwise addition, the dehydration condensation reaction was carried out for 5 hours while maintaining the temperature at 50 to 55° C. under a nitrogen atmosphere; when the absence of 9-fluorenone was determined by thin layer chromatography (TLC), the reaction was completed. Methanol was added; also, 33% by weight of aqueous sodium hydroxide solution was slowly added dropwise until the reaction system became alkaline. Then, the reaction mixture was heated to 80° C. and continued stirring for about 30 minutes; next, it was filtered after cooling. Finally, the filtered crude product was placed in a acetone/methanol mixed solution, and was subjected to recrystallization treatment to obtain 44.38 g of a white solid 9,9-bis(3-phenyl-4-(2-hydroxyethoxy)phenyl)fluorene product with a yield of about 90%.

In this example, a high performance reverse liquid chromatography (Dionex UltiMate 3000) was used for detection and purity analysis. Liquid chromatographic conditions were Agilent Polaris 5 C18-A 250×4.6 mm, mobile phase 95% acetonitrile-5% aqueous solution, UV detection wavelength 254 nm, flow rate 1.0 mL/min, column temperature at 30° C., and injection volume for 20 μL. The purity algorithm was calculated as [actual compound weight (instrument value)/crude product weight (weighed value)]*100%. The purity was 97.6%.

The 9,9-bis(3-phenyl-4-(2-hydroxyethoxy)phenyl)fluorene product was dissolved in an acetone solvent according to the standard test method of ASTM-D1209 to prepare a concentration of 10% by weight. The sample liquid was colorimetrically measured using a chromatic aberration meter (hunterLac Color Quest XE) and a platinum-cobalt standard solution (APHA color values of 5, 10, 15, 30, 50, 100, 500, respectively), and the 9,9-bis(3-phenyl-4-(2-hydroxyethoxy)phenyl)fluorene product was measured for APHA color value of 17.

Example 2

9-fluorenone (10 g, 55.49 mmole), 2-[(2-phenyl)phenoxy]ethanol (24.96 g, 214.26 mmole) and toluene (8.67 g) were placed in a reaction flask, and heated to about 50 to 55° C. to completely dissolve the above reactants. The 3-mercaptopropionic acid (0.58 g, 5.46 mmole) was added, and then methanesulfonic acid (21.32 g, 221.83 mmole) was added dropwise at a dropping rate of 0.16-0.24 ml/min. After the completion of the dropwise addition, the first dehydration condensation reaction was carried out for 4 hours at a temperature of from 50 to 55° C. under a nitrogen atmosphere; then, methanesulfonic acid (5.33 g, 55.46 mmole) was added dropwise at a constant dropping rate of 0.12 ml/min; and while maintaining a temperature of 50 to 55° C., the second dehydration condensation reaction for 4 hours under nitrogen atmosphere was carried out; when the absence of 9-fluorenone was determined by thin layer chromatography (TLC), the reaction was completed. Methanol was added; also, 33% by weight aqueous sodium hydroxide solution was slowly added dropwise until the reaction system became alkaline. Then, the reaction mixture was heated to 80° C. and continued stirring for about 30 minutes; next, it was filtered after cooling. Finally, the filtered crude product was placed in an acetone/methanol mixed solution, and was subjected to recrystallization treatment for two times. The purity and chromaticity value were measured by the test method of Example 1.

In the present example, 28.61 g of a white solid 9,9-bis (3-phenyl-4-(2-hydroxyethoxy)phenyl)fluorene product was obtained. The yield was about 87%, and the purity was 99.6%, with APHA color value of 9.

It can be seen from the above that in Example 2, the catalyst was introduced twice and the recrystallization process was repeated. Compared with Example 1, the impurities were completely removed, the purity of the product was 99.6%, and the chroma quality was improved.

Example 3

9-fluorenone (5 g, 27.75 mmole), 2-[(2-phenyl)phenoxy] ethanol (12.48 g, 58.25 mmole) and toluene (4.34 g) were placed in a reaction flask, which was heated to 50 to 55° C. to completely dissolve the above reactant. 3-mercaptopropionic acid (0.29 g, 2.73 mmole) was added, and then methanesulfonic acid (10.66 g, 110.91 mmole) was added dropwise at a dropping rate of 0.08-0.12 ml/min. After the completion of the dropwise addition, the first dehydration condensation reaction was carried out for 8 hours while maintaining the temperature at 50 to 55° C. under a nitrogen atmosphere; then, methanesulfonic acid (2.67 g, 27.78 mmole) was added dropwise at a constant dropping rate of 0.06 ml/min; and while maintaining a temperature of 50 to 55° C., a second dehydration condensation reaction for 4 hours under nitrogen atmosphere was carried out; when the absence of 9-fluorenone by thin layer chromatography (TLC) was determined, the reaction was completed. Methanol was added; also, 33% by weight aqueous sodium hydroxide solution was slowly added dropwise until the reaction system became alkaline. Then, the reaction mixture was heated to 80° C. and continued stirring for about 30 minutes; next, it was filtered after cooling. Finally, the filtered crude product was placed in an acetone/methanol mixed solution, and was subjected to recrystallization treatment; and the purity and chromaticity values were measured by the test method of Example 1.

In the present example, 14.51 g of a 9,9-bis(3-phenyl-4-(2-hydroxyethoxy)phenyl)fluorene product as a white solid was obtained with a yield of about 89%. 98.5%, APHA color value is 20.

Example 4

The preparation method was the same as in Example 3, except that the methylsulfonic acid content (12 g, 124.87 mmole) of the first dehydration condensation reaction and the methylsulfonic acid content of the second dehydration condensation reaction (1.33 g, 13.84 mmole).

In the present example, 14.50 g of a white solid 9,9-bis (3-phenyl-4-(2-hydroxyethoxy)phenyl)fluorene product was obtained with a yield of about 89% and purity of 98.8%, with APHA color value of 18.

Example 5

9-fluorenone (15 g, 83.24 mmole), 2-[(2-phenyl)phenoxy] ethanol (37.45 g, 174.79 mmole) and toluene (13 g) were placed in a reaction flask, which was heated to from about 50 to 55° C. to completely dissolve the above reactants. 3-mercaptopropionic acid (0.88 g, 8.29 mmole) was added, and methanesulfonic acid (8.0 g, 83.2 mmole) was added dropwise at a constant rate of 0.18 ml/min. After the completion of the dropwise addition, the first dehydration condensation reaction was carried out for 4 hours while maintaining the temperature at 50 to 55° C. under a nitrogen atmosphere; then, methanesulfonic acid (32 g, 332.95 mmole) was added dropwise at a constant dropping rate of 0.3 ml/min; while maintaining a temperature of 50 to 55° C., the second dehydration condensation reaction for 4 hours under nitrogen atmosphere was carried out; when the absence of 9-fluorenone by thin layer chromatography (TLC) was determined, the reaction was completed. Methanol was added; also, 33% by weight aqueous sodium hydroxide solution was slowly added dropwise until the reaction system became alkaline. Then, the reaction mixture was heated to 80° C. and continued stirring for about 30 minutes; next, it was filtered after cooling. Finally, the filtered crude product was placed in an acetone/methanol mixed solution, and was subjected to recrystallization treatment; and the purity and chromaticity values were measured by the test method of Example 1.

In the present example, 42.74 g of a white solid 9,9-bis (3-phenyl-4-(2-hydroxyethoxy)phenyl)fluorene product was obtained with a yield of about 87% and purity of 99.3%, with APHA color value of 16.

As can be seen from the above, in Examples 2, 3, 4, and 5, the catalyst was fed twice, and compared with Example 1, the side reaction was also inhibited, and the effect of product purity was significantly improved.

Example 6

9-fluorenone (10 g, 55.49 mmole), 2-[(2-phenyl)phenoxy] ethanol (24.97 g, 116.54 mmole) and toluene (8.67 g) were placed in a reaction flask, which was heated to about 50 to 55° C. to completely dissolve the above reactant. A mixture solution of 3-mercaptopropionic acid (0.59 g, 5.55 mmol) and methanesulfonic acid (26.66 g, 277.42 mmol) was added dropwise at a dropping rate of 0.16-0.24 ml/min. After the completion of the dropwise addition, the solution is maintained at a temperature of 50 to 55° C. and a nitrogen atmosphere for 8 hours; when the absence of 9-fluorenone by thin layer chromatography (TLC) was determined, the reaction was completed. Methanol was added; also, 33% by weight aqueous sodium hydroxide solution was slowly added dropwise until the reaction system became alkaline. Then, the reaction mixture was heated to 80° C. and continued stirring for about 30 minutes; next, it was filtered after cooling. Finally, the filtered crude product was placed in an acetone/methanol mixed solution, and was subjected to recrystallization treatment; and the purity and chromaticity values were measured by the test method of Example 1.

In the present example, 27.2 g of a white solid 9,9-bis(3-phenyl-4-(2-hydroxyethoxy)phenyl)fluorene product was obtained with a yield of about 83% and purity of 98.9%, with APHA color value of 19.

Example 7

9-fluorenone (10 g, 55.49 mmole), 2-[(2-phenyl)phenoxy] ethanol (24.97 g, 116.54 mmole) and toluene (8.67 g) were placed in a reaction flask, which was heated to 40 to 45° C. to completely dissolve the above reaction. 3-mercaptopropionic acid (0.58 g, 5.55 mmole) was added, and then methanesulfonic acid (21.32 g, 221.83 mmole) was added dropwise at a dropping rate of 0.16-0.24 ml/min. After the completion of the dropwise addition, the first dehydration condensation reaction was carried out for 4 hours while maintaining the temperature at 40 to 45° C. under a nitrogen atmosphere; then, methanesulfonic acid (5.33 g, 55.46 mmole) was added dropwise at a constant dropping rate of 0.12 ml/min; the second dehydration condensation reaction was carried out at a temperature of 40 to 45° C. under a nitrogen atmosphere for 7 hours; when the absence of 9-fluorenone by thin layer chromatography (TLC) was determined, the reaction was completed. Methanol was added; also, 33% by weight aqueous sodium hydroxide solution was slowly added dropwise until the reaction system became alkaline. Then, the reaction mixture was heated to 80° C. and continued stirring for about 30 minutes; next, it was filtered after cooling. Finally, the filtered crude product is placed in an acetone/methanol mixed solution, and was subjected to recrystallization treatment; and the purity and chromaticity values were measured by the test method of Example 1.

In the present example, 28.8 g of a white solid 9,9-bis(3-phenyl-4-(2-hydroxyethoxy)phenyl)fluorene product was obtained with a yield of about 88% and purity of 99.4%, with APHA color value of 14.

Comparative Example 1

The preparation method was the same as in Example 1, except that the amount of 2-[(2-phenyl)phenoxy]ethanol was used (44.58 g, 208.07 mmole), and sulfuric acid (36.74 g, 374.59 mmole) was used as a catalyst. The dehydration condensation reaction time was 3 hours.

In the present example, 49 g of a white solid 9,9-bis(3-phenyl-4-(2-hydroxyethoxy)phenyl)fluorene product was obtained with a yield of about 99% and the purity of 45.12%, and due to poor solubility, the color cannot be measured.

It can be seen from the results of the above examples that the preparation method of the present disclosure can effectively inhibit the formation of sulfonation or sulfonate by-products by using an alkylsulfonic acid as a catalyst, as compared with the comparative example 1. In the case of a small amount of 2-[(2-phenyl)phenoxy]ethanol reactant, an effect of improving product yield and purity was brought about.

Given the foregoing, the bisphenol fluorene compound of the present disclosure is prepared by using an alkylsulfonic acid as a catalyst and a mercapto-containing compound as a co-catalyst, thereby effectively inhibiting the formation of by-products and improving the yield and purity of the product. Further, the method of the present disclosure has high conversion rate, so that a relatively smaller amount of the 2-[(2-phenyl)phenoxy]ethanol reactant can be used, thereby effectively reducing the cost of the process raw material and eliminating the problem of recovering the excess reactants. The obtained product has the characteristics of low chroma, high purity, high yield and low cost, and has industrial applicability.

The above examples are merely illustrative, and are not intended to limit the present disclosure. Modifications and variations of the above-described examples can be made by a person skilled in the art without departing from the spirit and scope of the present disclosure. Therefore, the scope of the present disclosure is defined by the scope of the appended claims. As long as the effects and implementation purposes of the present disclosure are not affected, they should be encompassed in the technical disclosure.

What is claimed is:

1. A method for preparing 9,9-bis(3-phenyl-4-(2-hydroxyethoxy)phenyl)fluorene, comprising:
   adding a mercapto-containing compound as a co-catalyst to a reaction system having 9-fluorenone and 2-[(2-phenyl)phenoxy]ethanol; and
   adding alkylsulfonic acid as a catalyst to the reaction system containing the co-catalyst to carry out a dehydration condensation reaction of the 9-fluorenone and the 2-[(2-phenyl)phenoxy]ethanol to obtain the 9,9-bis(3-phenyl-4-(2-hydroxyethoxy)phenyl)fluorene.

2. The method of claim 1, wherein a molar ratio of the 2-[(2-phenyl)phenoxy]ethanol to the 9-fluorenone is from 2 to 4.

3. The method of claim 1, wherein the catalyst is added to the reaction system in multiple stages at a temperature of from 40° C. to 80° C.

4. The method of claim 3, wherein the catalyst is added dropwise to the reaction system, and when the catalyst is added, a temperature change of the reaction system is less than 10° C.

5. The method of claim 1, wherein a molar ratio of the catalyst to the 9-fluorenone is from 3 to 9.

6. The method of claim 1, wherein the catalyst is added in a two-stage manner after the addition of the co-catalyst to the reaction system.

7. The method of claim 6, wherein the catalyst is added in a first stage and the dehydration condensation reaction is carried out for 4 to 8 hours, and the catalyst is then added in an amount in a second stage, and wherein the dehydration condensation reaction is carried out for 4 to 8 hours.

8. The method of claim 1, wherein the alkylsulfonic acid has a molecular formula R—$SO_3H$, wherein R is a C1-C3 alkyl group.

9. The method of claim 1, wherein the catalyst is methanesulfonic acid, and a molar ratio of the methanesulfonic acid to the 9-fluorenone is from 3 to 9.

10. The method of claim 1, wherein the mercapto-containing compound is at least one selected from the group consisting of a mercaptan containing a C1-C10 alkylene group or a C6-C12 arylene group and a mercaptocarboxylic acid containing a C1-C10 alkylene group or a C6-C12 arylene group.

11. The method of claim 10, wherein the mercaptocarboxylic acid having the C1-C10 alkylene group or the C6-C12 arylene group is 3-mercaptopropionic acid, mercaptoacetic acid or mercaptobenzoic acid.

12. The method of claim 1, wherein a molar ratio of the co-catalyst to the 9-fluorenone is from 0.05 to 0.2.

13. The method of claim 1, wherein the dehydration condensation reaction is carried out at a temperature of from 40° C. to 80° C. and for a reaction time of from 4 to 12 hours.

14. The method of claim 1, further comprising dissolving the 9-fluorenone and the 2-[(2-phenyl)phenoxy]ethanol in a reaction solvent before adding the co-catalyst.

15. The method of claim 14, wherein the reaction solvent is an aromatic hydrocarbon solvent or a halogenated alkane.

16. The method of claim 15, wherein the aromatic hydrocarbon solvent comprises at least one selected from the group consisting of benzene, toluene, xylene and trimethylbenzene.

17. The method of claim 15, wherein the halogenated alkane comprises at least one selected from the group consisting of dichloromethane, chloroform and carbon tetrachloride.

18. The method of claim 14, wherein the reaction solvent is in an amount of from 10 to 20% by weight, based on a total weight of the 9-fluorenone and the 2-[(2-phenyl)phenoxy]ethanol.

19. The method of claim 1, further comprising performing recrystallization after completion of the dehydration condensation reaction.

20. The method of claim 19, wherein in the recrystallization, a mixed solution of methanol and acetone is used as a recrystallization solvent.

* * * * *